United States Patent [19]

Ford et al.

[11] Patent Number: 4,775,745

[45] Date of Patent: Oct. 4, 1988

[54] DIAZONIUM COMPOUNDS USEFUL AS COMPONENTS FOR NUCLEIC ACID PROBES

[75] Inventors: John P. Ford, Tappan; Bernard F. Erlanger, Whitestone, both of N.Y.; C. William Blewett, Ft. Mitchell, Ky.

[73] Assignee: National Distillers and Chemical Corporation, New York, N.Y.; by said C. W. Blewett

[21] Appl. No.: 939,370

[22] Filed: Dec. 8, 1986

[51] Int. Cl.$^4$ ................. C07C 113/00; C07C 113/04
[52] U.S. Cl. ........................ 534/560; 436/63; 436/501; 436/532; 436/544; 436/546; 436/804; 436/828; 514/150; 534/558; 534/562; 534/563; 534/564; 534/565; 546/146; 546/262; 548/303; 548/478; 548/492; 549/70; 549/72; 549/483; 549/487; 564/183; 564/184; 564/186
[58] Field of Search ............... 534/560, 558, 562, 563, 534/564, 565; 548/303; 514/150

[56] References Cited

U.S. PATENT DOCUMENTS

| | | | |
|---|---|---|---|
| 2,744,116 | 5/1956 | Shreve et al. | 534/560 X |
| 3,637,672 | 1/1972 | Seino et al. | 534/560 X |
| 3,715,872 | 2/1973 | Stempel et al. | 534/560 X |
| 4,539,148 | 9/1985 | Yamamoto et al. | 534/560 X |
| 4,556,513 | 12/1985 | Shibahara et al. | 534/560 |
| 4,617,621 | 10/1986 | Sheldon et al. | 548/303 X |

OTHER PUBLICATIONS

Britten et al, Scientific American, vol. 222, No. 4, pp. 24 to 31 (1968).
Forster et al, Nucleic Acid Research, vol. 13, No. 3, pp. 745 to 761 (1985).
Green, Adv. Protein Chem., vol. 29, pp. 85 to 133 (1975).
Landegent et al, Experimental Cell Research, vol. 153, pp. 61 to 72 (1984).
Leary et al, Proc. Nat'l. Acad. Sci. U.S.A., vol. 80, pp. 4045 to 4049 (1983).
Novak et al, Proc. Nat'l. Acad. Sci. U.S.A., vol. 83, pp. 586 to 590 (1986).
Stellwag et al, Nucleic Acid Research, vol. 8, pp. 299 to 317 (1980).
Tchen et al, Proc. Nat'l. Acad. Sci. U.S.A., vol. 81, pp. 3466 to 3470 (1984).
Ward et al, Proc. Nat'l. Acad. Sci. U.S.A., vol. 79, pp. 4381 to 4385 (1982).

*Primary Examiner*—Floyd D. Higel
*Attorney, Agent, or Firm*—Pennie & Edmonds

[57] ABSTRACT

This invention relates to a diazonium compound of the formula:

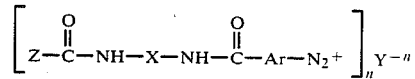

wherein
Z is selected from the group consisting of biotin, an antigen, an antibody, a photoreactive group, a fluorescent group and heavy metal-containing compounds;
X is an alkylene group containing up to 18 carbon atoms in the principle chain and a total of up to 24 carbon atoms or a substituted alkylene group containing up to 18 carbon atoms in the principle chain with substituents selected from the group consisting of solubility-enhancing groups and cleavable —S—S— containing moieties;
Ar is an unsubstituted or substituted aryl or heteroaryl; and
Y is an anion and n is an integer from 1-3.

Such compounds are useful as components for nucleic acid probes.

4 Claims, 2 Drawing Sheets

DIAZONIUM COMPOUNDS USEFUL AS COMPONENTS FOR NUCLEIC ACID PROBES

FIELD OF THE INVENTION

This invention relates to the field of nucleic acid detection by means of non-radioactive reagents. More specifically, the invention discloses a group of diazonium compounds that are particularly useful as components in a non-radioactive nucleic acid hybridization detection system.

BACKGROUND OF THE INVENTION

The technique of nucleic acid hybridization has been successfully employed for the study of DNA structure nucleic acid purification, gene localization, and detection and diagnosis of diseases and mutations.

Hybridization assays are based on the structural properties of DNA molecules. The DNA of most organisms is comprised of two strands of polynucleotides which are associated by means of noncovalent interactions (e.g. hydrogen bonding, stacking forces, etc.) into the familiar double helical structure. It was demonstrated by Britten, et al. (*Sci. American* 222(4): 24–31 (1968)) that under certain conditions it was possible to cause the two strands to separate from one another. This process of strand separation has been variously referred to as unwinding, denaturing or melting of the double-stranded duplex. It was further discovered that under a second set of conditions the strands would reassociate to reform the duplex DNA structure, this process being referred to as reassociation or renaturation. By measuring the kinetics of reassociation, estimates were able to be made of the relative amounts of unique sequence DNA to repetitive or reiterated DNA sequences.

Further studies demonstrated it was possible to denature the DNAs from two different sources (e.g. two different species of bacteria, two different types of animals or plants) then mix the two populations of single stranded nucleic acids and under renaturation conditions estimate the percentage of double stranded hybrids that were formed; such being an indication of sequence homology between the two sources. The double-stranded molecules formed by the reassociation of one strand from a first source and another strand from a second source are known as a hybrid DNA molecules and the process of forming such molecules is known as DNA hybridization. In a related embodiment a small nucleotide segment comprising a fragment of a single gene up to a size which would include several genes may be used to hybridize to DNA sample for the purposes of identifying if a complementary segment exists in the sample as well as its localization within the sample. The segment is often of predetermined sequence or function and is generally referred to as a nucleic acid hybridization probe. These probes have become extremely important as reagents for the detection of specific nucleic acid sequences. Commonly the probes are labelled with radioactive isotopes to facilitate their analytical detection. The isotopes normally employed include $^{32}P$, $^{125}I$ or $^3H$; however, considerations regarding stability, safety, ease of detection and disposal of waste have fostered the development of non-isotopically labelled probe molecules.

One approach has been to detect nucleic acids by immunological means, either by developing antibodies which will discriminate between single and double stranded DNAs or by labelling the nucleic acid with an immunoreactive component such as a hapten. Landegert, et al. (*Exp. Cell Res.* 153: 61–72 (1984)) and Tchen et al. (*Proc. Nat'l Acad. Sci. USA* 81: 3466–3470 (1984)) have employed N-acetoxy-N-2-acetylaminofluorene to develop immunogenic probes the detection of which is by classical direct or indirect enzyme-linked immunosorbent assays (ELISA). Because of the carcinogenic nature and attendant disposal problems associated with N-acetoxy-N-2-acetylaminofluorene, alternative methods are desired.

A hapten which has gained widespread use for labelling nucleic acid molecules is the vitamin, biotin. Of particular advantage is the high affinity ($K_d = 10^{-15}M$) displayed for biotin by the glycoprotein avidin (Green, N. M., *Adv. Protein Chem.* 29: 85–133 (1975)). Subsequently it was found that avidin could be reacted with enzymes, fluorescent groups or electron dense molecules to form analytically detectable avidin-conjugates. Ward, et al. (*Proc. Nat'l Acad. Sci. USA* 79: 4381–4385 (1982) and *Proc. Nat'l Acad. Sci. USA* 80: 4045–4049 (1983)) have developed a method for the enzymatic incorporation of biotin-labelled analogs of dUTP and UTP into nucleic acids. Although these methods have been quite useful, different types of nucleic acids require modifications of the protocol, and the method requires expensive substrates and enzyme which made large scale preparation economically disadvantageous. It was desirable, therefore, to develop chemical methods for labelling nucleic acid with biotin. Several attempts to develop chemical labelling methods have been reported.

Manning et al. (*Chromosoma* 53: 107–117 (1975)) have disclosed the chemical cross-linking of a biotin labelled cytochrome c conjugate to RNA with formaldehyde. M. Renz and C. Kurz substituted enzymes such as peroxidase or alkaline phosphatase for cytochrome c in a similar cross-linking proce-dure (*Nucleic Acid Res.* 12(8): 3435–3444 (1984)).

These methods have been associated with problems of instability of the conjugates under hybridization conditions or the steric hindrance of hybridization itself.

Finally, Forster, et al. (*Nucleic Acid Res.* 13(3): 745–761 (1985)) have disclosed the synthesis of a photoactivatable biotin analog of the formula:

which may be used to label M13 DNA probes. However, this compound reacts with both single and double stranded DNA and as pointed out by the authors, this dual reactivity limits the extent of probe modification possible without interfering with the hybridization of target sequences by single stranded regions of the probe.

BRIEF DESCRIPTION OF THE INVENTION

This invention relates to a diazonium compound of the formula:

wherein

Z is selected from the group consisting of biotin, a hapten, an antigen, an antibody, a photoreactive group, a fluorescent group and a heavy metal-containing compound;

X is an alkylene group containing up to 18 carbon atoms in the principal chain and a total of up to 24 carbon atoms and may be substituted with solubility- enhancing groups and/or cleavable —S—S— containing moieties;

Ar is an unsubstituted or substituted aryl or heteroaryl; and

Y is an anion.

This invention also relates to a non-radioactively labelled nucleic acid probe comprising a single-stranded DNA virus or phage containing a region of heterologous DNA complementary to the nucleic acid to be detected, said viral DNA having covalently attached thereto a diazonium-linked signal molecule.

In a further embodiment the invention provides a method for preparing a probe for the detection of a specific nucleic acid sequence comprising:
providing a nucleic acid sequence complementary to the sequence to be detected;
integrating said complementary sequence into a single-stranded virus to form a probe;
reversibly blocking the complementary sequence;
labelling the unblocked viral nucleic acid with a diazonium-derivatized signal molecule; and
unblocking the complementary nucleic acid sequence.

In yet another embodiment the invention provides a method for the detection of a specific nucleic acid sequence comprising:
hybridizing to the sequence to be detected a probe having covalently attached thereto a diazonium linked analytically detectable group, and indicating the presence of the hybrid by detecting the analytically detectable group.

In yet another embodiment the invention provides a method for detecting duplex DNA containing single base mismatches comprising:
forming a duplex DNA molecule containing at least one single base mismatch;
reacting said mismatched duplex DNA with a diazonium compound of the formula:

wherein

Z is selected from the group consisting of biotin, a hapten, an antigen, an antibody, a photoreactive group, a fluorescent group and a heavy metal-containing compound;

X is an alkylene group containing up to 18 carbon atoms in the principle chain and a total of up to 24 carbon atoms and may be substituted with substituents selected from the group consisting of solubility-enhancing groups and cleavable —S—S— containing moieties;

Ar is an unsubstituted or substituted aryl or heteroaryl; and

Y is an anion and identifying said reacted mismatch duplex DNA by detecting the Z group.

In yet another embodiment the invention provides a method for purifying perfectly matched heteroduplex DNA comprising
(a) forming a mixture of perfectly matched and imperfectly matched heteroduplex DNA
(b) reacting the mixture with a diazonium compound of the formula:

to label the imperfectly matched heteroduplexes;
(c) separating the labelled imperfectly matched heteroduplex DNA from the unlabelled perfectly matched heteroduplex DNA.

In a final embodiment the invention provides a method for preparing compounds of the formula comprising:
reacting p-nitrobenzoic acid with a methylene diamine to form the nitrobenzoylamide of the diamine; converting the nitrobenzoylamide to the aminobenzoylamide by hydrogenation over palladium/charcoal; forming the N' Biotinyl N⁶ (p-aminobenzoyl) diamine derivative by reacting the aminobenzoylamide diamine with a hydroxy succinimide ester of biotin; and converting the biotin diamine derivative to a diazonium by reaction with NaNO₂ and acid to yield the compound of the formula above.

DETAILED DESCRIPTION OF THE FIGURES

DETAILED DESCRIPTION OF THE INVENTION

This invention provides a rapid, easily employed reagent for the chemical labelling of DNA with non-isotopic analytically detected moieties. Reagents useful in practicing this invention are diazonium compounds which have been derivatized.

The derivative molecules can be conceptualized as consisting of three regions:

Dioazonium compounds are particularly useful as ractive functionalities for DNA. Such compounds are known to react most strongly with unpaired guanine residues and to a lesser extent with thymine and adenine residues in DNA (Stellwag, E. J. and A. E. Dahlberg, Nucleic Acid Res. 8:299 (1980)). Although this reactivity is important as it provides a convenient means to derivatization of nucleic acids, to be useful as a component of a non-radioactive probe, the diazonium compound itself must include funciionalities serving as analyticalydeterctable moieties.

Analytically detectable moieties include, but are not limited to, biotin, haptens, antigens, antibodies, a photoreactive group, a fluoroescent groups such as Texas Red, fluorscein, rhodamine, phycoerythrins and heavy metal-containing compounds such as ferritin. The analytically detectable groups should permit easy, reliable, and sensitive detection, should not interfere with the hybridization process nor be chemically affected thereby, and should be assayable following hybridization under conditions in which the hybrid is maintained.

The analytically detectable group is beneficially separated from the diazonium functionality by means of a molecular spacer. The spacer is preferably an alkylene group consisting of up to 18 carbon atoms in the principle chain and a total of up to 24 atoms and may be substituted with solubility enhancing groups such as substituted and unsubstituted quaternary amines and/or cleavable —S—S— containing moieties.

The diazonium group is linked to the spacer by means of an aryl or heteroaryl functionality. The aryl groups may have from 6 to 10 carbons and include phenyl and α- and β-naphthyl. The aryl groups may contain non-reactive substituents such as alkyl, hydroxy, alkoxy, hydroxyalkyl, mercapto, alkylmercapto, mercaptoalkyl, halo, haloalkyl, aminoalkyl, nitro, methylenedioxy, and trifluoromethyl.

By non-reactive it is meant that substituents do not participate in the derivitization reaction under the conditions employed. In addition to the substituent not participating in the primary reactions, it is substantially incapable of forming undersirable secondary reactions.

The heteroaryl groups include aromatic ring systems containing one or more atoms other than carbon. These heteroaryl groups inclueε pyrrole, pyridine, imidazole, furan, furfuryl, thiophene, benzimidazole, thiazole, indole, quinoline, isoquinoline, and the like. These heterocyclic groups may also be substituted with groups as described for the aryl groups above.

Certain of the diazonium compounds are conveniently prepared by the following route:

wherein x is an integer from 1–24 and z is biotin, an antigen, a hapten, an antibody, a fluorescent group, a photoreactive group or a heavy-metal containing compound.

Provided the appropriate starting materials are available, compounds of this invention may also be prepared by the following alternate synthetic route:

-continued

The compounds exist as acid addition salts. These include salts of mineral acids such as hydrochloric, hydriodic, hydrobromic, phosphoric, metaphosporic, nitric and sulfuric acids, as well as salts of organic acids such as tartaric, acetic, citric, malic, benzoic, glycollic, gluconic, succinic, arylsulfonic, e.g., p-toluenesulfonic acids, and the like.

Of course the stoichiometry is a function of the acid used, hence the number of diazonium molecules is, for example, 1 when HCl is used, up to two when $H_2SO_4$ is employed and up to 3 when phosphoric acid is employed.

The details of the synthesis of some of these compounds are provided in Example 1.

Construction of Non-Radioactive Labelled Probe

Non-radioactive probe useful for the detection of nucleic acids can be prepared according to the following procedure.

DNA sequences corresponding to the target sequences are isolated from natural sources, chemically synthesized or isolated from a sample containing the sequences after cloning the DNA in an appropriate cloning vector/host system.

A portion of the target DNA sample is rendered single-stranded by denaturation and placed on a nitrocellulose filter. A second sample of the target DNA is incorporated in double stranded form into the RF form of a M-13 cloning vector. The M13 vector containing the target sequence is introduced into a suitable *E. coli* host by transformation. Recombinant virus is cultured in *E. coli* host and single stranded DNA is isolated from the virus particles. The single-stranded DNA is recovered as covalent closed-circle containing a region of target DNA. The M13 vectors are commercially available and detailed instructions for the cloning of DNA by means of the vectors as provided by the manufacturer (See for Example "M13 Cloning/Dideoxy Sequencing Instruction Manual", Bethesda Res. Lab. Life Techn. Inc., Gaithersburg, Md. 20877).

This single-stranded circle is hybridized to the single stranded target molecules that had been previously attached to the nitrocellulose filter. Since the hybridization is due to the complementary association of the target regions said region is functionally double stranded, while the remaining portion of the M13 vector remains single stranded. The hybridized complex is contacted with the diazonium reagent which reacts with unpaired, guanine, thymine and adenine residues of the M-13 vector.

The unreacted reagent is washed from the filter and the diazonium reagent labelled M13 molecule is eluted from the filter. The diazonium reagent labelled M13 may be used as a non-radioactive probe for example in a dot-blot assay system as described by Bresser J. et al. *DNA* 2:243–254 (1983). Accordingly, a sample of DNA containing the target sequence is isolated, denatured and attached to a nitrocellulose filter. The M13 probe reagent is added, and is bound to the filter by virtue of the hybridization reaction between the target sequence on the filter and its complement integrated within the M-13 reagent. Unreacted probe is removed by extensive washing of the filters. The presence of the analytically detectable group incorporated into the M13 probe through the diazotization reaction is then indicated by reaction with the appropriate reagents, for example if the group is biotin, it may be detected by reaction with enzyme-conjugated avidin or streptavidin followed by addition of a color forming substrate of the enzyme and detection of the colored product formed. Alternatively, if the analytically detectable group is a hapten or antigen, an antibody may be employed. This antibody may be conjugated directly to an enzyme and detected enzymatically as above, or the unconjugated antibody can be detected by a second anti-globulin that is enzymatically labelled.

If the analytically detectable group is a photoreactive group, fluorescent group or a heavy metal containing compound, they may be detected by the appropriate photoreaction, fluorescent or heavy metal detection technique.

The biotin-avidin or biotin-streptavidin detection system is preferred. In addition to the high affinity of avidin for biotin as mentioned above, avidin is tetrameric with respect to biotin and as such permits the formation of super molecular aggregates, thereby resulting in signal amplification.

Purification and Identification of DNA Containing Single Base Mismatches

In a further embodiment the diazonium compounds of this invention may be used to detect single base pair mismatches in DNA. If, after hybridization, the double stranded molecule contains a mispaired region of a single base pair or more in which an A, T or G base is unpaired, then reaction with the diazonium compound is possible. If the diazonium compound contains a biotin functionality, then an immobilized avidin support can be employed to capture the mismatched hybrids. If the immobilized avidin is used in a column, then a mixture of mismatch hybrids and perfectly matched DNA duplexes may be resolved. In this embodiment the mismatched sequences are reacted with a biotinylated diazonium compound (the perfectly matched duplexes are of course unreactive), the mixture is then poured through the avidin column and the biotinylated mismatch sequences are retained while the duplex DNA is washed through the matrix. As such this embodiment provides an improved method for gene purification. Of course if another analytically indicatable functionality is employed (e.g. antigen or hepten) then the column would be comprised of the appropriately immobilized antibody.

In yet a further embodiment the diazonium coupounds of this invention can be used to label mismatches after in situ hybridization experiments, where after the mismatches are labelled, the analytically detectable functionality can be detected by reaction with ferritin labelled avidin or antibody and then visualized by electron microscopy.

EXAMPLE 1

This Example describes the preparation and characterization of the precursor to a biotinylated diazonium salt useful as a nucleic acid labelling reagent.

1. Mono-p-nitrobenzoylamide of 1,6-hexanediamine monohydrochloride p-Nitrobenzoic acid ethyl ester (9.8 g, 0.05 mole) is added to a stirred solution of 1,6-hexamethylenediamine (29.95 g., 0.25 mole) in 62.5 ml abs. ethanol at room temperature (25° C.). After dissolving, the clear solution is kept at 37° C. in a stoppered flask for 20 hrs. The ethanol is removed in vacuo (rotating still, bath 37° C.) and the residue transferred to a separatory funnel with 250 ml of ethyl acetate and 250 ml of water. The water layer is removed and the ethyl acetate washed with three portions of 125 ml water to eliminate the excess diamine. The last washing is amine free. The ethyl acetate layer is dried over anh. sodium sulfate. Addition of a 7% solution of HCl gas in ethyl ether with stirring until slight acid (pH paper) (about 25 ml) precipitates the hydrochloride salt.

After cooling at +4° C. (overnight), the crystals are filtered in vacuo and washed on the filter with two portions of 50 ml ethyl acetate and two portions of 50 ml ethyl ether. The dry crude product weighs 8.43 g and has a m.p. of 174°-5° C. (yield 55.9%). After recrystallization from isopropanol (25 ml/gr), the m.p. rose to 176°-7° C.

Analysis: C=52.08, H=6.82, N=13.79, Cl=11.54. Theor. for $C_{13}H_{20}N_3O_3Cl$: C=51.74, H=6.68, N=13.92, Cl=11.75.

Spectrum in methanol has maxima at 264.5 nm (E=1.2×10$^4$) and 203 mm. TLC on SiO$_2$RP18-/MeOH:H$_2$O 3:1 shows only one spot Rf 0.04, U.V. absorbing and ninhydrin positive.

2. Mono-p-nitrobenzoylamide of 1,6-hexanediamine

The hydrochloride (3.018 g, 0.01 mole) is dissolved in 13 ml water and cooled to about 4° C. with an ice bath. While mixing with a glass rod, 2 ml of 5N sodium hydroxide is added slowly. An oil is precipitated and solidified as a mass of crystals under mixing and cooling. The water phase is discarded and the solid covered with 12 ml of water. After 2 hrs at +4° C., the solid is filtered in vacuo and washed with two 5 ml portions of water. It is dried in vacuo over NaOH pellets; yield 2.508 g of base, m.p. 57°-8° C. (94.5%).

3. Mono-p-aminobenzoylamide of 1,6-hexanediamine

The previously prepared mononitrobenzoylamide (1.46 g, 5.5 mmole) is dissolved in 40 ml of methanol at room temperature (25° C.). 0.170 g of palladium on charcoal (10% catalyst) is added and hydrogenation is conducted at 25° C. and atmospheric pressure. After a rapid absorption of 370 ml of H$_2$, the uptake stopped. 40 ml of methanol is added and the catalyst filtered in vacuo leaving an oil which crystallized as prisms with m.p. of 133°-4° C., yield 1.24 g (96%). Spectra (in NaOH) $E$max at 278.9 and 203.5 nm.

4. N$^1$-Biotinyl-N$^6$-(p-aminobenzoyl)hexanediamide

The mono-p-aminobenzoylamide of 1,6-hexanediamine (1.235 g 5.25 mmole) is dissolved in 10 ml of dimethylformamide at room temperature. D-Biotin hydroxysuccinimide ester (1.7 g, 5 mmole) is dissolved in 17 ml dimethylformamide at 50° C. After it is cooled to 25° C., the amine solution is added to it. DMF (3ml) is used to rinse the flask containing the aminine and this, too, is added to the biotin ester. The reaction flask is flushed with nitrogen and kept stoppered for 24 hours at 25° C. The reaction mixture remained clear. It is concentrated in vacuo (rot. evap. 40° C./2 mm) to 7.5 ml, and then added dropwise to 50 ml of acetonitrile to precipitate a jelly-like product; it is separated by centrifugation. The supernatant is decanted and the precipitate stirred twice with 50 ml acetonitrile followed by centrifugation (to eliminate excess amine). It is then stirred with ethyl ether and the gel, which crystallized, was filtered, washed with ethyl ether and dried in vacuo. Yield 1.98 g (86%) white crystals m.p. 167°-8° C. Spectra in methanol show maxima at 277.5 nm (E=1.66×10$^4$) and 203.9 nm.

TLC on SiO$_2$RP18/MeOH-H$_2$O 3:1: one spot Rf 0.66; ninhydrin negative.

Analysis: C=58.62, H=7.35, N=14.75, S=7.53.

For $C_{23}H_{35}N_5SO_3$: C=59.84, H=7.64, N=15.17, S=6.95.

NMR and mass spectroscopy are consistent with desired product.

5. N$^1$-Biotinyl-6-(p-aminobenzoyl) hexanediamide hydrochloride

N$^1$-Biotinyl-N$^6$-(p-aminobenzoyl) hexanediamide hydrochloride (1 g, 2.166 mmole) is dissolved in 50 ml methanol at 25° C. Cooled to +5° C. in an ice bath. Slowly added, under stirring, a 7% solution of HCl gas in ethyl ether until acid (pH paper) (about 1.25 ml required). The clear solution of the hydrochloride is precipitated by pouring to a stirred 350 ml of ethyl ether (cooled at +5° C.). After 1 hour, the precipitate was filtered, washed with ethyl ether and dried free of solvent and excess acid in vacuo over KOH pellets.

Yield 1.07 g of crystals, m.p. 192°-3° C.

The spectra in water has max at 270 nm. A 1.3 nM solution has pH 3.48.

Analysis: C=55.34, H=7.15, N=13.64, S=6.97, Cl=7.03. Theor. for $C_{23}H_{36}N_5O_3SCl$: C=55.46, H=7.29, N=14.06, S=6.44, Cl=7.12.

By substituting the cognate diamine and aryl or heteroaryl ester, and following the method above, the following additional compounds are prepared:

N$^1$-Biotinyl-N$^6$-[3-(5-amino)indoloyl]hexanediamide.

N$^1$-Biotinyl-N$^6$-[4-(8-amino-1-methoxy)isoquinolyl carbonyl]hexanediamide.

N$^1$-Biotinyl-N$^{10}$- [3-(7-amino-2-hydroxy)-quinolylcarbonyl]decanediamide.

N$^1$-Biotinyl-N$^8$-[4-(2-amino)thienoyl]octanediamide.

N$^1$-Biotinyl-N$^{18}$- [3-(4-amino furoyl]octadecanediame.

N$^1$-Biotinyl-N$^6$-[2-(6-amino)napthoyl]hexanediamide.

N$^1$-Biotinyl-N$^6$-[3-(5-amino)pyridylcarbonyl]hexanediamide.

N$^1$-Biotinyl-N$^6$-[2-methyl-4-aminobenzoyl]hexanediamide.

EXAMPLE 2

This example shows the ability of diazonium compounds of this invention to interact with unpaired nucleic acid bases.

A. Biotinylated diazonium compounds react with protruding (Sticky ends) but not flush ends of double stranded DNA. To convert the diamine compound of Example 1 to the diazonium compound, the diamine compound was suspended in either dimethyl formamide or water according to the following recipes formulations.

| A | B |
|---|---|
| 5 mg Reagent | 5 mg Reagent |
| 100λ DMF | 400λ H₂O |
| 300λ H₂O | 35λ 1MHCl |
| 35λ 1MHCl | |
| Heat for 1 min at 65° C. | Heat at 100° C. for 2 min |
| Add 100λ 0.1 M NaNO₂ | Centrifuged to remove |
| Place on ice | undissolved residue - |
| | 250λ recovered |
| | Add 62.5λ 0.1 M NaNO₂ |
| | Place on ice |

DNA (Promega Biotech-Psp65) after reaction with either Hae III or Sau 3a (50 ug of each enzyme as per manufacturer's suggested protocol) is resuspended in 30λ H₂O containing 0.1λ 0.5M EDTA.

Hae III is a restriction endonuclease that recognizes the sequence and produces flush ends.

Sau 3A is a restriction enzyme that recognizes the sequence produces GATC protruding ends.

Reaction mixtures were prepared as follows:

| Trial | DNA | H₂O | Diazonium Compound (AQ = Aqueous) (DMF = Dimethyl Formamide) | 1M NaMOPS (pH 7.5) | 0.2M Na Borate (pH 8.5) | Temperature of Incubation |
|---|---|---|---|---|---|---|
| 1 | Hae III 3λ | 20λ | 25λ DMF | 5λ | — | 24° C. |
| 2 | Hae III 3λ | — | 25λ DMF | — | 25λ | 24° C. |
| 3 | Hae III 3λ | 20λ | 25λ AQ | 5λ | — | 24° C. |
| 4 | Hae III 3λ | — | 25λ AQ | — | 25λ | 24° C. |
| 5 | Hae III 3λ | 20λ | 25λ DMF | 5λ | — | 30° C. |
| 6 | Hae III 3λ | — | 25λ DMF | — | 25λ | 30° C. |
| 7 | Hae III 3λ | — | — | — | — | — |
| 8 | Sau 3A 3λ | 20λ | 25λ DMF | 5λ | — | 24° C. |
| 9 | Sau 3A 3λ | — | 25λ DMF | — | 25λ | 24° C. |
| 10 | Sau 3A 3λ | 20λ | 25λ AQ | 5λ | — | 24° C. |
| 11 | Sau 3A 3λ | — | 25λ AQ | — | 25λ | 24° C. |
| 12 | Sau 3A 3λ | 20λ | 25λ DMF | 5λ | — | 30° C. |
| 13 | Sau 3A 3λ | — | 25λ DMF | — | 25λ | 30° C. |
| 14 | Sau 3A 3λ | — | — | — | — | — |

Figure 1:
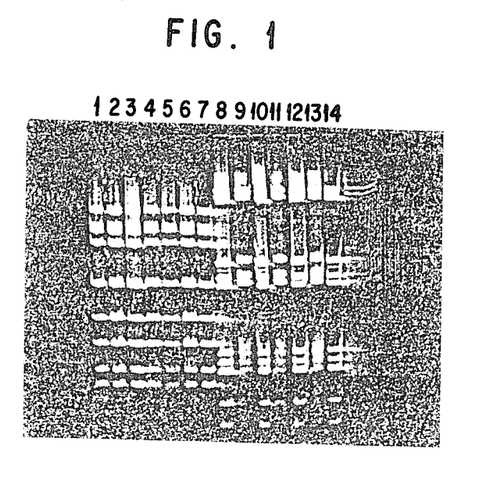
FIG. 1 illustrates the effect of the reactivity of a diazonium compound of the invention on the electrophoretic migration of DNAs containing protruding termini as opposed to flush-ended termini. Experimental details are provided in Example 2.

Samples were incubated for 2¼ hours at the temperature indicated. The reaction was stopped by the addition of 450 u 10.15 soium acetate pH 5.1. DNA was precipitated with 2 vols. of 100% ethanol, resuspended in 15 TAE buffer and 15% acrylamide gels were run for at 200 volts for 6 hr. and DNA visualized by staining with 0.5 μg/ml ethidium bromide as shown in FIG. 1. The diazonium compound reacted with the DNA containing protruding termini but not with DNA having flush ends as shown by comparing the absense of retardation of gel mobility when lanes 1-6 are compared to lane 7 as opposed to when lanes 8-13 are compared to lane 14 where the retardation is evident.

B. Biotinylated diazonium compounds react with streotavidin after bindino to DNA Reagent Preparation:
5 mg Diamine HCl compound of Example 1
100λ DMF
300λ H₂O
35λ 1MHCl Heated to 65° C. and 100 ul of 0.1M NaNO₂ added after 1 minute.

Labelling

A sample of single-stranded M13 with a 209 b.p. Sma I - Pst I fragment from the 5' end of Hras oncogene was rendered flush ended by Klenow fragment reaction and cloned into the Sma I site of M13x (Novack, et al PNAS 83:586-90 (1986))x at a concentration of 400 ng/λ in 0.01M Tris (pH 7.4) 0.001M EDTA was prepared.

A sample of double stranded Psp65 with 2 copies of 1.8 kb B-globin Bam H1 fragment digested with PvuII at a concentration of 1 μg/λ in 0.01M Tris (pH 7.4) 0.001M EDTA was also prepared.

In order to test the reactivity with streptavidin the following trials were prepared.

| Trial (Pvu-II) | 0.2 M Na Borate | 20 mM Diazonium Compound | H₂O | T209-M13 | PsP65 |
|---|---|---|---|---|---|
| 1 | 75λ | 40λ | — | 30λ | 5λ |
| 2 | 75λ | 4λ | 36λ | 30λ | 5λ |

Samples of each trial were taken at 5, 25, 120 minutes after incubation at room temperature. 450 of 0.15M Na Acetate (pH 5.1) was added. The DNAs were precipitated with 2 volumes of ethanol and resuspended in 50λ of TE buffer.

The DNA was detected by the following protocol as described in *Bethesda Research Laboratory* (BRL) product protocol.

1. 0.8% agarose gel were run in TBE
2. Ethidium bromide stained gel was photographed
3. Gel incubated in 100 ml of Buffer 1

Buffer 1
0.1M Tris (pH 7.4)
0.1M NaCl
2 mM MgCl₂
0.05% Triton

4. Added were 50 ml Buffer 1 and streptavidin at 2 ug/ml for 1½ hours at room temperature 5. Wash 2 times with Buffer 1 (100 ml at 37° C. for 30 minutes)
6. Add BRL alkaline phosphatase 1 μg/ml with Buffer 1 in 30 ml for 1 hour room temperature
7. Wash 2 times with Buffer 1 75 ml for 30 minutes
8. Wash 2 times with Buffer 2

Buffer 2
0.1M Tris (pH 9.5)
0.1M NaCl
50mM MgCl

9. Protect from light—Develop with 70% DMF g/ml NBT
40 μg/ml 5-bromo-4 chloro-3 indolyl phosphate The results of these trials are presented in FIG. 2. The lanes contained the following samples:

| Lane | | | | |
|---|---|---|---|---|
| 1 | 1.5 | | ssM13 | T209 (400 mg/λ) |
| 2 | 0.3 | | Pvu II | 4.8K, 3.0K |
| 3 | 5.3 | mM | Diazo-biotin | for 5 min. |
| 4 | 5.3 | mM | Diazo-biotin | for 25 min. |
| 5 | 5.3 | mM | Diazo-biotin | for 120 min. |
| 6 | 0.53 | mM | Diazo-biotin | for 5 min. |
| 7 | 0.53 | mM | Diazo-biotin | for 25 min. |
| 8 | 0.53 | mM | Diazo-biotin | for 120 min. |

Figure 2A:
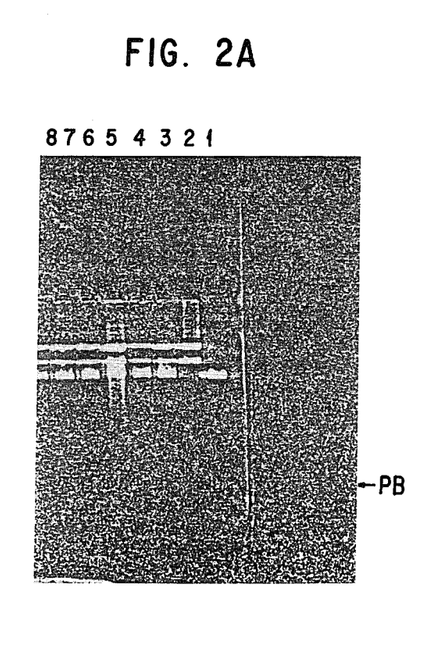
FIG. 2 illustrates the reactivity of biotinylated diazonium compounds with DNA and while retaining the ability to interact with enzymaticlaly-labeled strepavidin.
Figure 2B:
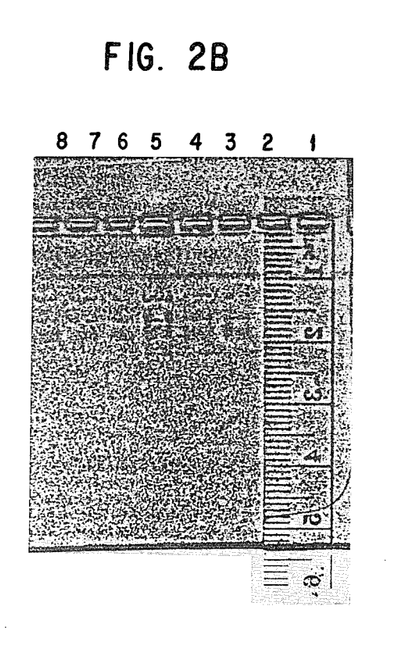

FIG. 2 (A) shows the results of ethidium bromide staining;

FIG. 2 (B) shows untreated ss and ds DNA is unreactive to strepavidin/biotinylated alkaline phosphatase while the single stranded diazonium reagent treated samples are highly reactivated.

EXAMPLE 3

This example illustrates the reactivity of the diazonium compounds of this invention with single base mismatches in DNA.

Figure 3:
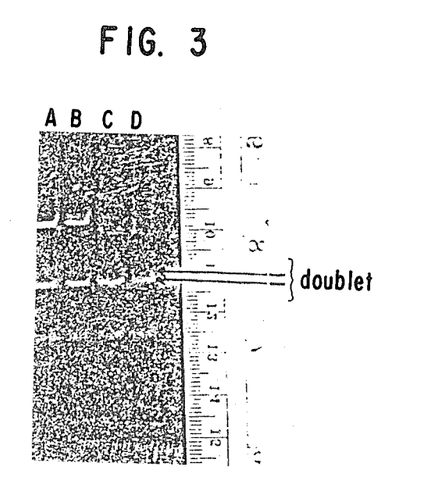
FIG. 3 illustrates the ability of a compound of the invention to detect the presence of single-base mismatches in DNA. Experimental details are provided in Example 3.

40 μg of M13 containing a 3716p insert was cloned in both orientation to generate the H-ras-heteroduplex (heteroduplex A as shown in FIG. 3 from Novack et al. supra) as well as the homoduplex controls. The DNAs were mixed and hybridized 42° for 1 hour in 100λ ETOH and resuspended in 35λ of H2O to form said heters and homo duplexes.

The DNAs were reacted with the diazonium compound of Example 2 for either 25 minutes at 16° C. or 120 minutes at 24° C. The reaction mixtures contained 40 of 20 mM diazonium compound, 35λ of DNA and 75λ of 0.2M Na borate buffer pH 8.5.

After the reaction, the samples were loaded on a 1ml Sepharase 6B-CL spin column and centrifuged on table top centrifuge as described by Maniatis et al. ("Molecular Cloning", Cold Spring Harbor Laboratory).

The samples were recovered and digested with Alu I endonuclease per manufacture's protocol generating three fragments:
(a) a 128 b.p. fragment with 6 b.p. loop
(b) a 77 b.p. fragment with G-T mismatch
(c) a 54 b.p. fragment with a T-C mismatch The fragments were analyzed on a 15 percent acrylamide gel as described by Novack et al. (supra).

With reference to FIG. 3, lanes A and B represent the homoduplex whereas lanes C and D contain the heteroduplex. The DNAs in lanes A and C were reacted with the diazonium compound for 2-5 minutes at 16° C. whereas the DNAs in lanes B & D were reacted for 120 minutes at 24° C.

The upper most set of bands represent the 128 b.p. fragment with the 6 b.p. loop, the bands are present in the homoduplex (no loop present) but the heteroduplex (loop present) was so reactive with the diazonium compounds that it was severly retarded and hence absent from the region of the gel shown.

The middle set of bands represent the 77 b.p. fragment with the G-T mismatch; the doublet present in lane D indicates that reactivity with diazonium compound has caused retardation of this species. No effects can be seen in the bottom set of bands, i.e. those containing the 54 b.p. fragment within T-C mismatch.

What is claimed is:

1. A diazonium salt of formula:

wherein z is selected from the group consisting of biotin, a hapten, an antigen, an antibody, a photoreactive group, a fluorescent group selected from the group consisting of Texas Red, fluorscein, rhodamine, phycoerythrins, and ferritin;

X is alkylene containing up to 18 carbon atoms in the principle chain and a total of up to 24 carbon atoms;

Ar is an aryl group selected from the group consisting of phenyl and alpha-and beta-naphthyl or a heteroaryl group selected from the group consisting of pyrrole, pyridine, imidazole, furan, furfuryl, thiophene, benzimidazole, thiazole, indole, quinoline and isoquioline wherein said aryl and said heteroaryl group is unsubstituted or substituted with a group selected from the group consisting of hydroxy, mercapto, halo, nitro, methylenedioxy and trifluoromethyl; and

Y is an anion and n is an integer from 1 to 3.

2. The diazonium compound according to claim 1, having the formula:

wherein in X, Y, n and have the meanings as in claim 1.

3. The diazonium compound according to claim 2 having the formula:

4. The diazonium compound according to claim 3 having the formula: